US 8,827,954 B2

(12) United States Patent
Dunn et al.

(10) Patent No.: US 8,827,954 B2
(45) Date of Patent: Sep. 9, 2014

(54) DEFLATABLE BIFURCATED DEVICE

(75) Inventors: Richard Dunn, Brooklyn Park, MN (US); Steve Hoff, Elk River, MN (US); Thomas Holman, Princeton, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 12/479,632

(22) Filed: Jun. 5, 2009

(65) Prior Publication Data
US 2010/0114019 A1    May 6, 2010

Related U.S. Application Data

(60) Provisional application No. 61/059,243, filed on Jun. 5, 2008.

(51) Int. Cl.
| A61M 31/00 | (2006.01) |
| A61M 37/00 | (2006.01) |
| A61F 2/954 | (2013.01) |
| A61M 25/10 | (2013.01) |
| A61F 2/958 | (2013.01) |
| A61M 29/00 | (2006.01) |
| A61F 2/06  | (2013.01) |
| A61F 2/856 | (2013.01) |

(52) U.S. Cl.
CPC ............ *A61M 25/1011* (2013.01); *A61F 2/954* (2013.01); *A61F 2002/065* (2013.01); *A61F 2250/0029* (2013.01); *A61M 25/1002* (2013.01); *A61F 2/958* (2013.01); *A61M 2025/1045* (2013.01); *A61F 2/856* (2013.01)
USPC .................. 604/103.06; 604/101.01; 623/1.35

(58) Field of Classification Search
CPC ............ A61M 25/10; A61M 25/1011; A61M 25/1002; A61M 2025/1002; A61M 2025/1004; A61M 2025/1031; A61M 2025/1045; A61M 2025/1059; A61M 2025/1086; A61M 2025/1088; A61M 2025/109; A61F 2/954; A61F 2/958; A61F 2/859; A61F 2250/0029; A61F 2002/065
USPC ............. 604/101.01–101.05, 103.06–103.14, 604/916, 919; 623/1.27–1.29, 1.35
See application file for complete search history.

(56) References Cited

U.S. PATENT DOCUMENTS

| 1,596,754 A | 8/1926 | Moschelle |
| 3,657,744 A | 4/1972 | Ersek |

(Continued)

FOREIGN PATENT DOCUMENTS

| CA | 2318314 | 7/1999 |
| DE | 9014845.2 | 1/1991 |

(Continued)

OTHER PUBLICATIONS

U.S. Appl. No. 12/479,611 to Richard A. Noddin et al., filed Jun. 5, 2009.

(Continued)

*Primary Examiner* — Bhisma Mehta
*Assistant Examiner* — Jenna Zhang
(74) *Attorney, Agent, or Firm* — Seager, Tufte & Wickhem LLC

(57) ABSTRACT

A medical device for insertion and expansion within a bifurcated lumen is described. An expansion region of the device has regions thereon which, in some cases, enable the device to fold into a predetermined configuration upon deflation. The regions may be defined by differing modulus of the device material.

10 Claims, 9 Drawing Sheets

(56) References Cited

U.S. PATENT DOCUMENTS

| | | |
|---|---|---|
| 3,872,893 A | 3/1975 | Roberts |
| 4,140,126 A | 2/1979 | Choudhury |
| 4,309,994 A | 1/1982 | Grunwald |
| 4,410,476 A | 10/1983 | Redding et al. |
| 4,413,989 A | 11/1983 | Schjeldahl et al. |
| 4,421,810 A | 12/1983 | Rasmussen |
| 4,453,545 A | 6/1984 | Inoue |
| 4,479,497 A | 10/1984 | Fogarty et al. |
| 4,503,569 A | 3/1985 | Dotter |
| 4,552,554 A | 11/1985 | Gould et al. |
| 4,681,570 A | 7/1987 | Dalton |
| 4,689,174 A | 8/1987 | Lupke |
| 4,731,055 A | 3/1988 | Melinyshyn et al. |
| 4,733,665 A | 3/1988 | Palmaz |
| 4,739,762 A | 4/1988 | Foote |
| 4,759,748 A | 7/1988 | Reed |
| 4,762,128 A | 8/1988 | Rosenbluth |
| 4,769,029 A | 9/1988 | Patel |
| 4,819,664 A | 4/1989 | Nazari |
| 4,872,874 A | 10/1989 | Taheri |
| 4,878,495 A | 11/1989 | Grayzel |
| 4,896,670 A | 1/1990 | Crittenden |
| 4,900,314 A | 2/1990 | Quackenbush |
| 4,906,244 A | 3/1990 | Pinchuk et al. |
| 4,909,258 A | 3/1990 | Kuntz et al. |
| 4,911,711 A | 3/1990 | Telfair et al. |
| 4,941,877 A | 7/1990 | Montano, Jr. |
| 4,946,464 A | 8/1990 | Pevsner |
| 4,957,501 A | 9/1990 | Lahille et al. |
| 4,957,508 A | 9/1990 | Kaneko et al. |
| 4,963,313 A | 10/1990 | Noddin et al. |
| 4,964,850 A | 10/1990 | Bouton et al. |
| 4,983,167 A | 1/1991 | Sahota |
| 4,994,071 A | 2/1991 | MacGregor |
| 5,042,976 A | 8/1991 | Ishitsu et al. |
| 5,054,501 A | 10/1991 | Chuttani et al. |
| 5,059,177 A | 10/1991 | Towne et al. |
| 5,061,240 A | 10/1991 | Cherian |
| 5,064,435 A | 11/1991 | Porter |
| 5,085,664 A | 2/1992 | Bozzo |
| 5,102,403 A | 4/1992 | Alt |
| 5,102,417 A | 4/1992 | Palmaz |
| 5,104,404 A | 4/1992 | Wolff |
| 5,117,831 A | 6/1992 | Jang et al. |
| 5,122,125 A | 6/1992 | Deuss |
| 5,135,536 A | 8/1992 | Hillstead |
| 5,147,317 A | 9/1992 | Shank et al. |
| 5,147,385 A | 9/1992 | Beck et al. |
| 5,156,785 A | 10/1992 | Zdrahala |
| 5,159,920 A | 11/1992 | Condon et al. |
| 5,192,297 A | 3/1993 | Hull |
| 5,195,970 A | 3/1993 | Gahara |
| 5,195,984 A | 3/1993 | Schatz |
| 5,211,683 A | 5/1993 | Maginot |
| 5,217,440 A | 6/1993 | Frassica |
| 5,222,971 A | 6/1993 | Willard et al. |
| 5,226,913 A | 7/1993 | Pinchuk |
| 5,234,457 A | 8/1993 | Andersen |
| 5,236,446 A | 8/1993 | Dumon |
| 5,257,974 A | 11/1993 | Cox |
| 5,263,932 A | 11/1993 | Jang |
| 5,304,220 A | 4/1994 | Maginot |
| 5,306,246 A | 4/1994 | Sahatjian et al. |
| 5,320,605 A | 6/1994 | Sahota |
| 5,324,257 A | 6/1994 | Osborne et al. |
| 5,334,153 A | 8/1994 | McIntyre et al. |
| 5,337,733 A | 8/1994 | Bauerfeind et al. |
| 5,338,300 A | 8/1994 | Cox |
| 5,342,295 A | 8/1994 | Imran |
| 5,342,297 A | 8/1994 | Jang |
| 5,342,387 A | 8/1994 | Summers |
| 5,350,395 A | 9/1994 | Yock |
| 5,382,472 A | 1/1995 | Yanidis et al. |
| 5,383,892 A | 1/1995 | Cardon et al. |
| 5,387,235 A | 2/1995 | Chuter |
| 5,395,332 A | 3/1995 | Resseman et al. |
| 5,395,334 A | 3/1995 | Keith et al. |
| 5,404,887 A | 4/1995 | Prather |
| 5,409,458 A | 4/1995 | Khairkhahan et al. |
| 5,413,581 A | 5/1995 | Goy |
| 5,413,586 A | 5/1995 | Dibie et al. |
| 5,417,208 A | 5/1995 | Winkler |
| 5,425,765 A | 6/1995 | Tiefenbrun et al. |
| 5,437,638 A | 8/1995 | Bowman |
| 5,443,497 A | 8/1995 | Venbrux |
| 5,445,624 A | 8/1995 | Jimenez |
| 5,449,373 A | 9/1995 | Pinchasik et al. |
| 5,449,382 A | 9/1995 | Dayton |
| 5,456,666 A | 10/1995 | Campbell et al. |
| 5,456,694 A | 10/1995 | Marin et al. |
| 5,456,712 A | 10/1995 | Maginot |
| 5,456,714 A | 10/1995 | Owen |
| 5,458,572 A | 10/1995 | Campbell et al. |
| 5,458,605 A | 10/1995 | Klemm |
| 5,462,530 A | 10/1995 | Jang |
| 5,476,471 A | 12/1995 | Shifrin et al. |
| 5,489,271 A | 2/1996 | Andersen |
| 5,489,295 A | 2/1996 | Piplani et al. |
| 5,496,292 A | 3/1996 | Burnham |
| 5,505,702 A | 4/1996 | Arney |
| 5,507,768 A | 4/1996 | Lau et al. |
| 5,507,769 A | 4/1996 | Marin et al. |
| 5,514,154 A | 5/1996 | Lau et al. |
| 5,514,178 A | 5/1996 | Torchio |
| 5,522,801 A | 6/1996 | Wang |
| 5,531,788 A | 7/1996 | Dibie et al. |
| 5,545,132 A | 8/1996 | Fagan et al. |
| 5,549,553 A | 8/1996 | Ressemann et al. |
| 5,549,554 A | 8/1996 | Miraki |
| 5,562,620 A | 10/1996 | Klein et al. |
| 5,562,724 A | 10/1996 | Vorwerk et al. |
| 5,562,725 A | 10/1996 | Schmitt et al. |
| 5,562,726 A | 10/1996 | Chuter |
| 5,569,295 A | 10/1996 | Lam |
| 5,571,087 A | 11/1996 | Ressemann et al. |
| 5,575,771 A | 11/1996 | Walinsky |
| 5,575,817 A | 11/1996 | Martin |
| 5,575,818 A | 11/1996 | Pinchuk |
| 5,591,228 A | 1/1997 | Edoga |
| 5,593,442 A | 1/1997 | Klein |
| 5,607,444 A | 3/1997 | Lam |
| 5,609,605 A | 3/1997 | Marshall et al. |
| 5,609,625 A | 3/1997 | Piplani et al. |
| 5,609,627 A | 3/1997 | Goicoechea et al. |
| 5,609,629 A | 3/1997 | Fearnot et al. |
| 5,613,949 A | 3/1997 | Miraki |
| 5,613,980 A | 3/1997 | Chauhan |
| 5,613,981 A | 3/1997 | Boyle et al. |
| 5,617,878 A | 4/1997 | Taheri |
| 5,626,600 A | 5/1997 | Horzewski et al. |
| 5,628,788 A | 5/1997 | Pinchuk |
| 5,632,762 A | 5/1997 | Myler |
| 5,632,763 A | 5/1997 | Glastra |
| 5,632,772 A | 5/1997 | Alcime et al. |
| 5,634,902 A | 6/1997 | Johnson et al. |
| 5,639,278 A | 6/1997 | Dereume et al. |
| 5,643,340 A | 7/1997 | Nunokawa |
| 5,653,743 A | 8/1997 | Martin |
| 5,662,614 A | 9/1997 | Edoga |
| 5,669,924 A | 9/1997 | Shaknovich |
| 5,669,932 A | 9/1997 | Fischell et al. |
| 5,674,197 A | 10/1997 | van Muiden et al. |
| 5,676,696 A | 10/1997 | Marcade |
| 5,676,697 A | 10/1997 | McDonald |
| 5,679,400 A | 10/1997 | Tuch |
| 5,683,451 A | 11/1997 | Lenker et al. |
| 5,690,642 A | 11/1997 | Osborne et al. |
| 5,693,084 A | 12/1997 | Chuter |
| 5,693,086 A | 12/1997 | Goicoechea et al. |
| 5,693,088 A | 12/1997 | Lazarus |
| 5,697,971 A | 12/1997 | Fischell et al. |
| 5,707,354 A | 1/1998 | Salmon et al. |
| 5,709,713 A | 1/1998 | Evans et al. |
| 5,716,365 A | 2/1998 | Goicoechea et al. |

(56) References Cited

U.S. PATENT DOCUMENTS

| | | |
|---|---|---|
| 5,716,617 A | 2/1998 | Khandke et al. |
| 5,718,683 A | 2/1998 | Ressemann et al. |
| 5,718,724 A | 2/1998 | Goicoechea et al. |
| 5,720,735 A | 2/1998 | Dorros |
| 5,723,004 A | 3/1998 | Dereume et al. |
| 5,724,977 A | 3/1998 | Yock et al. |
| 5,728,158 A | 3/1998 | Lau et al. |
| 5,733,303 A | 3/1998 | Israel et al. |
| 5,735,893 A | 4/1998 | Lau et al. |
| 5,746,766 A | 5/1998 | Edoga |
| 5,749,825 A | 5/1998 | Fischell et al. |
| 5,749,848 A | 5/1998 | Jang et al. |
| 5,755,734 A | 5/1998 | Richter et al. |
| 5,755,735 A | 5/1998 | Richter et al. |
| 5,755,770 A | 5/1998 | Ravenscroft |
| 5,755,771 A | 5/1998 | Penn et al. |
| 5,755,778 A | 5/1998 | Kleshinski |
| 5,759,172 A | 6/1998 | Weber et al. |
| 5,762,631 A | 6/1998 | Klein |
| 5,776,101 A | 7/1998 | Goy |
| 5,776,161 A | 7/1998 | Globerman |
| 5,776,180 A | 7/1998 | Goicoechea et al. |
| 5,782,906 A | 7/1998 | Marshall et al. |
| 5,797,947 A | 8/1998 | Mollenauer |
| 5,800,450 A | 9/1998 | Lary et al. |
| 5,800,508 A | 9/1998 | Goicoechea et al. |
| 5,814,061 A | 9/1998 | Osborne et al. |
| 5,817,126 A | 10/1998 | Imran |
| 5,824,008 A | 10/1998 | Bolduc et al. |
| 5,824,036 A | 10/1998 | Lauterjung |
| 5,824,040 A | 10/1998 | Cox et al. |
| 5,824,041 A | 10/1998 | Lenker et al. |
| 5,824,044 A | 10/1998 | Quiachon et al. |
| 5,827,320 A | 10/1998 | Richter et al. |
| 5,833,650 A | 11/1998 | Imran |
| 5,836,966 A | 11/1998 | St. Germain |
| 5,837,008 A | 11/1998 | Berg et al. |
| 5,838,856 A | 11/1998 | Lee |
| 5,843,031 A | 12/1998 | Hermann et al. |
| 5,843,160 A | 12/1998 | Rhodes |
| 5,843,164 A | 12/1998 | Frantzen et al. |
| 5,846,204 A | 12/1998 | Solomon |
| 5,851,210 A | 12/1998 | Torossian |
| 5,851,464 A | 12/1998 | Davila et al. |
| 5,853,389 A | 12/1998 | Hijlkema |
| 5,855,600 A | 1/1999 | Alt |
| 5,855,601 A | 1/1999 | Bessler et al. |
| 5,865,178 A | 2/1999 | Yock |
| 5,868,777 A | 2/1999 | Lam |
| 5,871,536 A | 2/1999 | Lazarus |
| 5,871,537 A | 2/1999 | Holman et al. |
| 5,891,133 A | 4/1999 | Murphy-Chutorian |
| 5,897,588 A | 4/1999 | Hull et al. |
| 5,906,640 A | 5/1999 | Penn et al. |
| 5,907,893 A | 6/1999 | Zadno-Azizi et al. |
| 5,913,895 A | 6/1999 | Burpee et al. |
| 5,913,897 A | 6/1999 | Corso, Jr. et al. |
| 5,921,958 A | 7/1999 | Ressemann et al. |
| 5,922,020 A | 7/1999 | Klein et al. |
| 5,928,248 A | 7/1999 | Acker |
| 5,938,682 A | 8/1999 | Hojeibane et al. |
| 5,938,696 A | 8/1999 | Goicoechea et al. |
| 5,948,016 A | 9/1999 | Jang |
| 5,951,599 A | 9/1999 | McCrory |
| 5,961,548 A | 10/1999 | Shmulewitz |
| 5,967,986 A | 10/1999 | Cimochowski et al. |
| 5,972,018 A | 10/1999 | Israel et al. |
| 6,007,517 A | 12/1999 | Anderson |
| 6,013,054 A | 1/2000 | Jiun Yan |
| 6,013,091 A | 1/2000 | Ley et al. |
| 6,017,324 A | 1/2000 | Tu et al. |
| 6,017,363 A | 1/2000 | Hojeibane |
| 6,024,763 A | 2/2000 | Lenker et al. |
| 6,030,414 A | 2/2000 | Taheri |
| 6,033,434 A | 3/2000 | Borghi |
| 6,033,435 A | 3/2000 | Penn et al. |
| 6,036,682 A | 3/2000 | Lange et al. |
| 6,039,749 A | 3/2000 | Marin et al. |
| 6,042,597 A | 3/2000 | Kveen et al. |
| 6,045,557 A | 4/2000 | White et al. |
| 6,048,361 A | 4/2000 | Von Oepen |
| 6,056,775 A | 5/2000 | Borghi et al. |
| 6,059,823 A | 5/2000 | Holman et al. |
| 6,059,824 A | 5/2000 | Taheri |
| 6,066,168 A | 5/2000 | Lau et al. |
| 6,068,655 A | 5/2000 | Seguin et al. |
| 6,071,285 A | 6/2000 | Lashinski et al. |
| 6,086,611 A | 7/2000 | Duffy et al. |
| 6,090,127 A | 7/2000 | Globerman |
| 6,090,128 A | 7/2000 | Douglas |
| 6,090,133 A | 7/2000 | Richter et al. |
| 6,096,073 A | 8/2000 | Webster et al. |
| 6,099,497 A | 8/2000 | Adams et al. |
| 6,117,117 A | 9/2000 | Mauch |
| 6,117,156 A | 9/2000 | Richter et al. |
| 6,126,685 A | 10/2000 | Lenker et al. |
| 6,129,738 A | 10/2000 | Lashinski et al. |
| 6,129,754 A | 10/2000 | Kanesaka et al. |
| 6,142,973 A | 11/2000 | Carleton et al. |
| 6,152,945 A | 11/2000 | Bachinski et al. |
| 6,165,195 A | 12/2000 | Wilson et al. |
| 6,165,197 A | 12/2000 | Yock |
| 6,165,214 A | 12/2000 | Lazarus |
| 6,179,867 B1 | 1/2001 | Cox |
| 6,183,506 B1 | 2/2001 | Penn et al. |
| 6,183,509 B1 | 2/2001 | Dibie |
| 6,190,403 B1 | 2/2001 | Fischell et al. |
| 6,193,746 B1 | 2/2001 | Strecker |
| 6,203,569 B1 | 3/2001 | Wijay |
| 6,210,380 B1 | 4/2001 | Mauch |
| 6,210,429 B1 | 4/2001 | Vardi et al. |
| 6,217,527 B1 | 4/2001 | Selmon et al. |
| 6,217,608 B1 | 4/2001 | Penn et al. |
| 6,221,080 B1 | 4/2001 | Power |
| 6,221,090 B1 | 4/2001 | Wilson |
| 6,221,098 B1 | 4/2001 | Wilson et al. |
| 6,231,563 B1 | 5/2001 | White et al. |
| 6,231,598 B1 | 5/2001 | Berry et al. |
| 6,231,600 B1 | 5/2001 | Zhong |
| 6,235,051 B1 | 5/2001 | Murphy |
| 6,241,762 B1 | 6/2001 | Shanley |
| 6,258,073 B1 | 7/2001 | Mauch |
| 6,258,099 B1 | 7/2001 | Mariero et al. |
| 6,258,116 B1 | 7/2001 | Hojeibane |
| 6,258,121 B1 | 7/2001 | Yang et al. |
| 6,261,273 B1 | 7/2001 | Ruiz |
| 6,261,305 B1 | 7/2001 | Marotta et al. |
| 6,261,319 B1 | 7/2001 | Kveen et al. |
| 6,264,682 B1 | 7/2001 | Wilson et al. |
| 6,273,911 B1 | 8/2001 | Cox et al. |
| 6,273,913 B1 | 8/2001 | Wright et al. |
| 6,287,314 B1 | 9/2001 | Lee et al. |
| 6,290,673 B1 | 9/2001 | Shanley |
| 6,293,967 B1 | 9/2001 | Shanley |
| 6,299,634 B1 | 10/2001 | Bergeron |
| 6,302,906 B1 | 10/2001 | Goicoechea et al. |
| 6,309,412 B1 | 10/2001 | Lau et al. |
| 6,309,414 B1 | 10/2001 | Rolando et al. |
| 6,312,459 B1 | 11/2001 | Huang et al. |
| 6,325,821 B1 | 12/2001 | Gaschino et al. |
| 6,325,826 B1 | 12/2001 | Vardi et al. |
| 6,334,870 B1 | 1/2002 | Ehr et al. |
| 6,346,089 B1 | 2/2002 | Dibie |
| 6,350,278 B1 | 2/2002 | Lenker et al. |
| 6,355,060 B1 | 3/2002 | Lenker et al. |
| 6,358,266 B1 | 3/2002 | Bonutti |
| 6,361,544 B1 | 3/2002 | Wilson et al. |
| 6,361,555 B1 | 3/2002 | Wilson |
| 6,371,978 B1 | 4/2002 | Wilson |
| 6,383,213 B2 | 5/2002 | Wilson et al. |
| 6,383,215 B1 | 5/2002 | Sass |
| 6,387,120 B2 | 5/2002 | Wilson et al. |
| 6,395,018 B1 | 5/2002 | Castaneda |
| 6,398,792 B1 | 6/2002 | O'Connor |

(56) References Cited

U.S. PATENT DOCUMENTS

| | | |
|---|---|---|
| 6,398,804 B1 | 6/2002 | Spielberg |
| 6,428,567 B2 | 8/2002 | Wilson et al. |
| 6,428,568 B2 | 8/2002 | Gaudoin et al. |
| 6,428,570 B1 | 8/2002 | Globerman |
| 6,432,133 B1 | 8/2002 | Lau et al. |
| 6,436,104 B2 | 8/2002 | Hojeibane |
| 6,436,134 B2 | 8/2002 | Richter et al. |
| 6,468,302 B2 | 10/2002 | Cox et al. |
| 6,475,208 B2 | 11/2002 | Mauch |
| 6,478,816 B1 | 11/2002 | Kveen et al. |
| 6,482,211 B1 | 11/2002 | Choi |
| 6,485,511 B2 | 11/2002 | Lau et al. |
| 6,494,905 B1 | 12/2002 | Zedler et al. |
| 6,508,836 B2 | 1/2003 | Wilson et al. |
| 6,511,504 B1 | 1/2003 | Lau et al. |
| 6,511,505 B2 | 1/2003 | Cox et al. |
| 6,520,988 B1 | 2/2003 | Colombo et al. |
| 6,527,799 B2 | 3/2003 | Shanley |
| 6,540,719 B2 | 4/2003 | Bigus et al. |
| 6,540,779 B2 | 4/2003 | Richter et al. |
| 6,572,647 B1 | 6/2003 | Supper et al. |
| 6,579,309 B1 | 6/2003 | Loos et al. |
| 6,579,312 B2 | 6/2003 | Wilson et al. |
| 6,582,394 B1 | 6/2003 | Reiss et al. |
| 6,582,459 B1 | 6/2003 | Lau et al. |
| 6,596,020 B2 | 7/2003 | Vardi et al. |
| 6,596,022 B2 | 7/2003 | Lau et al. |
| 6,599,315 B2 | 7/2003 | Wilson |
| 6,599,316 B2 | 7/2003 | Vardi et al. |
| 6,602,284 B2 | 8/2003 | Cox et al. |
| 6,641,609 B2 | 11/2003 | Globerman |
| 6,645,241 B1 | 11/2003 | Strecker |
| 6,652,573 B2 | 11/2003 | Von Oepen |
| 6,669,717 B2 | 12/2003 | Marotta et al. |
| 6,676,667 B2 | 1/2004 | Mariero et al. |
| 6,679,911 B2 | 1/2004 | Burgermeister |
| 6,689,156 B1 | 2/2004 | Davidson et al. |
| 6,692,483 B2 | 2/2004 | Vardi et al. |
| 6,695,877 B2 | 2/2004 | Brucker et al. |
| 6,706,062 B2 | 3/2004 | Vardi et al. |
| 6,709,440 B2 | 3/2004 | Callol et al. |
| 6,736,841 B2 | 5/2004 | Musbach et al. |
| 6,770,092 B2 | 8/2004 | Richter |
| 6,780,174 B2 | 8/2004 | Mauch |
| 6,802,856 B2 | 10/2004 | Wilson |
| 6,827,735 B2 | 12/2004 | Greenberg |
| 6,827,736 B2 | 12/2004 | Perouse |
| 6,835,203 B1 | 12/2004 | Vardi et al. |
| 6,852,124 B2 | 2/2005 | Cox et al. |
| 6,855,125 B2 | 2/2005 | Shanley |
| 6,890,349 B2 | 5/2005 | McGukin, Jr. et al. |
| 6,908,477 B2 | 6/2005 | McGukin, Jr. et al. |
| 6,942,689 B2 | 9/2005 | Majercak |
| 6,962,602 B2 | 11/2005 | Vardi et al. |
| 6,989,025 B2 | 1/2006 | Burgmeier et al. |
| 7,004,963 B2 | 2/2006 | Wang et al. |
| 7,056,323 B2 | 6/2006 | Mariero et al. |
| 7,105,019 B2 | 9/2006 | Hojeibane |
| 7,118,593 B2 | 10/2006 | Davidson et al. |
| 7,125,419 B2 | 10/2006 | Sequin et al. |
| 7,163,553 B2 | 1/2007 | Limon |
| 7,220,275 B2 | 5/2007 | Davidson et al. |
| 7,238,197 B2 | 7/2007 | Sequin et al. |
| 7,244,853 B2 | 7/2007 | Schreiber et al. |
| 7,252,679 B2 | 8/2007 | Fischell et al. |
| 7,344,557 B2 | 3/2008 | Yadin |
| 7,387,639 B2 | 6/2008 | Bourang et al. |
| 7,585,317 B2 | 9/2009 | Davidson et al. |
| 2001/0012927 A1 | 8/2001 | Mauch |
| 2001/0016767 A1 | 8/2001 | Wilson et al. |
| 2001/0016768 A1 | 8/2001 | Wilson et al. |
| 2001/0027291 A1 | 10/2001 | Shanley |
| 2001/0027338 A1 | 10/2001 | Greenberg |
| 2001/0029396 A1 | 10/2001 | Wilson et al. |
| 2001/0037116 A1 | 11/2001 | Wilson et al. |
| 2001/0037138 A1 | 11/2001 | Wilson et al. |
| 2001/0037140 A1 | 11/2001 | Gaudoin et al. |
| 2001/0037146 A1 | 11/2001 | Lau et al. |
| 2001/0037147 A1 | 11/2001 | Lau et al. |
| 2001/0039395 A1 | 11/2001 | Mariero et al. |
| 2001/0039448 A1 | 11/2001 | Dibie |
| 2001/0041927 A1 | 11/2001 | Solem |
| 2001/0047201 A1 | 11/2001 | Cox et al. |
| 2001/0049552 A1 | 12/2001 | Richter et al. |
| 2001/0056297 A1 | 12/2001 | Hojeibane |
| 2002/0013618 A1 | 1/2002 | Marotta et al. |
| 2002/0013619 A1 | 1/2002 | Shanley |
| 2002/0022874 A1 | 2/2002 | Wilson |
| 2002/0026232 A1 | 2/2002 | Marotta et al. |
| 2002/0032478 A1 | 3/2002 | Boekstegers et al. |
| 2002/0035392 A1 | 3/2002 | Wilson |
| 2002/0042650 A1 | 4/2002 | Vardi et al. |
| 2002/0052648 A1 | 5/2002 | McGukin, Jr. et al. |
| 2002/0058990 A1 | 5/2002 | Jang |
| 2002/0072790 A1 | 6/2002 | McGuckin, Jr. et al. |
| 2002/0107564 A1 | 8/2002 | Cox et al. |
| 2002/0111675 A1 | 8/2002 | Wilson |
| 2002/0123790 A1 | 9/2002 | White et al. |
| 2002/0123797 A1 | 9/2002 | Majercak |
| 2002/0123798 A1 | 9/2002 | Burgermeister |
| 2002/0151959 A1 | 10/2002 | Von Oepen |
| 2002/0156516 A1 | 10/2002 | Vardi et al. |
| 2002/0156517 A1 | 10/2002 | Perouse |
| 2002/0165604 A1 | 11/2002 | Shanley |
| 2002/0173835 A1 | 11/2002 | Bourang et al. |
| 2002/0173840 A1 | 11/2002 | Brucker et al. |
| 2002/0177892 A1 | 11/2002 | Globerman |
| 2002/0183763 A1 | 12/2002 | Callol et al. |
| 2002/0193872 A1 | 12/2002 | Trout, III et al. |
| 2002/0193873 A1 | 12/2002 | Brucker et al. |
| 2003/0004535 A1 | 1/2003 | Musbach et al. |
| 2003/0009209 A1 | 1/2003 | Hojeibane |
| 2003/0009214 A1 | 1/2003 | Shanley |
| 2003/0014102 A1 | 1/2003 | Hong et al. |
| 2003/0023301 A1 | 1/2003 | Cox et al. |
| 2003/0028211 A1 | 2/2003 | Crocker et al. |
| 2003/0050688 A1 | 3/2003 | Fischell et al. |
| 2003/0055378 A1 | 3/2003 | Wang et al. |
| 2003/0074047 A1 | 4/2003 | Richter |
| 2003/0093109 A1 | 5/2003 | Mauch |
| 2003/0114912 A1 | 6/2003 | Sequin et al. |
| 2003/0114915 A1 | 6/2003 | Mariero et al. |
| 2003/0125791 A1 | 7/2003 | Sequin et al. |
| 2003/0125799 A1 | 7/2003 | Limon |
| 2003/0125802 A1 | 7/2003 | Callol et al. |
| 2003/0144683 A1 | 7/2003 | Sirhan et al. |
| 2003/0163148 A1 | 8/2003 | Wang et al. |
| 2004/0015227 A1 | 1/2004 | Vardi et al. |
| 2004/0072849 A1 | 4/2004 | Schreiber et al. |
| 2004/0117003 A1 | 6/2004 | Ouriel et al. |
| 2004/0133223 A1 | 7/2004 | Weber |
| 2004/0133268 A1 | 7/2004 | Davidson et al. |
| 2004/0138737 A1 | 7/2004 | Davidson et al. |
| 2004/0148006 A1 | 7/2004 | Davidson et al. |
| 2004/0225318 A1 | 11/2004 | Eidenschink et al. |
| 2005/0015046 A1 | 1/2005 | Weber et al. |
| 2005/0015108 A1 | 1/2005 | Williams et al. |
| 2005/0027344 A1 | 2/2005 | Eidenschink |
| 2005/0060027 A1 | 3/2005 | Khenansho et al. |
| 2005/0102019 A1* | 5/2005 | Yadin ............ 623/1.11 |
| 2005/0102023 A1 | 5/2005 | Yadin et al. |
| 2005/0177130 A1 | 8/2005 | Konstantino et al. |
| 2006/0182873 A1* | 8/2006 | Klisch et al. ............ 427/2.1 |
| 2007/0067018 A1* | 3/2007 | Miller ............ 623/1.16 |
| 2007/0191923 A1 | 8/2007 | Weber et al. |
| 2008/0097302 A1 | 4/2008 | Chen |
| 2008/0109060 A1 | 5/2008 | Yadin |
| 2008/0114294 A1* | 5/2008 | Holman et al. ............ 604/96.01 |
| 2008/0125706 A1 | 5/2008 | Sutermeister et al. |
| 2008/0243221 A1* | 10/2008 | Arcand ............ 623/1.11 |

(56) References Cited

U.S. PATENT DOCUMENTS

FOREIGN PATENT DOCUMENTS

| | | |
|---|---|---|
| DE | 29701758 | 3/1997 |
| EP | 0551179 | 7/1993 |
| EP | 0646365 | 4/1995 |
| EP | 0684022 | 11/1995 |
| EP | 0804907 | 11/1997 |
| EP | 0876805 | 11/1998 |
| EP | 0884028 | 12/1998 |
| EP | 0891751 | 1/1999 |
| EP | 0897698 | 2/1999 |
| EP | 0897700 | 2/1999 |
| EP | 0904745 | 3/1999 |
| EP | 1031328 | 8/2000 |
| EP | 1031330 | 8/2000 |
| EP | 1157674 | 11/2001 |
| EP | 1254644 | 11/2002 |
| FR | 2678508 | 1/1993 |
| WO | WO 88/06026 | 8/1988 |
| WO | WO 90/13332 | 11/1990 |
| WO | WO 91/12779 | 9/1991 |
| WO | WO 92/19308 | 11/1992 |
| WO | WO 94/26180 | 11/1994 |
| WO | WO 95/08965 | 4/1995 |
| WO | WO 95/21592 | 8/1995 |
| WO | WO 96/29955 | 10/1996 |
| WO | WO 96/41592 | 12/1996 |
| WO | WO 97/09946 | 3/1997 |
| WO | WO 97/16217 | 5/1997 |
| WO | WO 97/26936 | 7/1997 |
| WO | WO 97/32544 | 9/1997 |
| WO | WO 97/33532 | 9/1997 |
| WO | WO 97/41803 | 11/1997 |
| WO | WO 97/45073 | 12/1997 |
| WO | WO 98/17204 | 4/1998 |
| WO | WO 98/19628 | 5/1998 |
| WO | WO 98/35634 | 8/1998 |
| WO | WO 98/36709 | 8/1998 |
| WO | WO 98/37833 | 9/1998 |
| WO | WO 98/44871 | 10/1998 |
| WO | WO 98/48733 | 11/1998 |
| WO | WO 98/52497 | 11/1998 |
| WO | WO 99/15103 | 4/1999 |
| WO | WO 99/17680 | 4/1999 |
| WO | WO 99/24104 | 5/1999 |
| WO | WO 99/34749 | 7/1999 |
| WO | WO 99/36002 | 7/1999 |
| WO | WO 99/39661 | 8/1999 |
| WO | WO 99/58059 | 11/1999 |
| WO | WO 99/65419 | 12/1999 |
| WO | WO 00/00104 | 1/2000 |
| WO | WO 00/12166 | 3/2000 |
| WO | WO 00/13613 | 3/2000 |
| WO | WO 00/53122 | 9/2000 |
| WO | WO 00/74595 | 12/2000 |
| WO | WO 01/21095 | 3/2001 |
| WO | WO 01/21109 | 3/2001 |
| WO | WO 01/21244 | 3/2001 |
| WO | WO 01/70299 | 9/2001 |
| WO | WO 02/068012 | 9/2002 |
| WO | WO 02/076333 | 10/2002 |
| WO | WO 02/094336 | 11/2002 |
| WO | WO 03/055414 | 7/2003 |
| WO | WO 2004/026180 | 4/2004 |
| WO | WO 2005/046757 | 5/2005 |
| WO | WO 2005/122958 | 12/2005 |
| WO | 2006014631 | 2/2006 |
| WO | WO 2006/053106 | 5/2006 |
| WO | 2008024220 | 2/2008 |

OTHER PUBLICATIONS

Caputo et al., "Stent Jail: A Minimum-Security Prison," The American Journal of Cardiology, vol. 77, pp. 1226-1230, Jun. 1, 1996.
Carrie et al., "'T'-Shaped Stent Placement: A Technique for the Treatment of Dissected Bifurcation Lesions," Catheterization and Cardiovascular Diagnosis, vol. 37, pp. 311-313, 1996.
Chevalier et at., "Placement of Coronary Stents in Bifurcation Lesions by the 'Culotte' Technique," The American Journal of Cardiology, vol. 82, pp. 943-949, Oct. 15, 1998.
Colombo et al., "'Kissing' Stents for Bifurcational Coronary Lesion," Catheterization and Cardiovascular Diagnosis, vol. 30, pp. 327-330, 1993.
Dichek et al., "Seeding of Intravascular Stents with Genetically Engineered Endothelial Cells," Circulation, vol. 80, No. 5, pp. 1347-1353, Nov. 1989.
Fischman et al., "A Randomized Comparison of Coronary-Stent Placement and Balloon Angioplasty in the Treatment of Coronary Artery Disease," New England Journal of Medicine, vol. 331, No. 8, pp. 496-501, Aug. 25, 1994.
Katoh et al., "New Double Wire Technique to Stent Ostial Lesions," Catheterization and Cardiovascular Diagnosis, vol. 40, pp. 400-402, 1997.
"Laser", Wikipedia, the free encyclopedia, http://en.wikipedia.org./wiki/Laser, printed Mar. 21, 2006, 11 pages.
Lewis et al., "Acute Procedural Results in the Treatment of 30 Coronary Artery Bifurcation Lesions with a Double-Wire Atherectomy Technique for Side-Branch Protection," American Heart Journal, vol. 127, No. 6, pp. 1600-1607, 1994.
Nakamura et al., "Techniques for Palmaz-Schatz Stent Deployment in Lesions with a Large Side Branch," Catheterization and Cardiovascular Diagnosis, vol. 34, pp. 353-361, 1995.
Satler et al. "Bifurcation Disease: To Treat or Not to Treat," Catheterization and Cardiovascular Interventions, vol. 50, pp. 411-412, 2000.
Serruys et al., "A Comparison of Balloon Expandable-Stent Implantation with Balloon Angioplasty in Patients with Coronary Artery Disease," The New England Journal of Medicine, vol. 331, No. 8, pp. 489-495, Aug. 25, 1994.
Yamashita et al., "Bifurcation Lesions: Two Stents Versus One Stent—Immediate and Follow-up Results," Journal of the American College of Cardiology, vol. 35, No. 5, pp. 1145-1151, Apr. 2000.

\* cited by examiner

DEFLATABLE BIFURCATED DEVICE

CROSS REFERENCE TO RELATED APPLICATIONS

This application claims priority to U.S. Provisional Application No. 61/059,243 filed on Jun. 5, 2008, the entire contents of which is hereby incorporated by reference.

This application is related to U.S. application Ser. No. 11/599,049, filed Nov. 14, 2007, and U.S. application Ser. No. 12/479,611 filed on even date herewith, which claims the benefit of U.S. Provisional Application Ser. No. 61/059,250 field Jun. 5, 2008, the entire contents of all of which are hereby incorporated by reference.

TECHNICAL FIELD

This disclosure relates to the treatment of bifurcated lumens with a balloon.

BACKGROUND

The body includes various passageways including blood vessels such as arteries, and other body lumens. These passageways sometimes become occluded or weakened. For example, they can be occluded by a tumor, restricted by plaque, or weakened by an aneurysm. When this occurs, the passageway can be reopened or reinforced, or even replaced, with a medical endoprosthesis. An endoprosthesis is an artificial implant that is typically placed in a passageway or lumen in the body. Many endoprostheses are tubular members, examples of which include stents, stent-grafts, and covered stents.

Many endoprostheses can be delivered inside the body by a catheter. Typically the catheter supports a reduced-size or compacted form of the endoprosthesis as it is transported to a desired site in the body, for example, the site of weakening or occlusion in a body lumen. Upon reaching the desired site, the endoprosthesis is installed so that it can contact the walls of the lumen.

One method of installation involves expanding the endoprosthesis. The expansion mechanism used to install the endoprosthesis may include forcing it to expand radially. For example, the expansion can be achieved with a catheter that carries a balloon in conjunction with a balloon-expandable endoprosthesis reduced in size relative to its final form in the body. The balloon is inflated to deform and/or expand the endoprosthesis in order to fix it at a predetermined position in contact with the lumen wall. The balloon can then be deflated, and the catheter withdrawn.

Body lumens often include bifurcated regions with branching pathways. Treatments, such as angioplasty and stent delivery, are sometimes required at locations proximate the branching physiology. A balloon configured for use with a bifurcated endoprosthesis can have a non-linear portion that expands the bifurcated portion of the endoprosthesis. It is desirable that upon deflation, the balloon forms a predictable low profile configuration that facilitates withdrawal from the body and is not likely to become caught on the endoprosthesis during removal.

SUMMARY

The following summary is provided to facilitate an understanding of some of the innovative features unique to the present disclosure and is not intended to be a full description. A full appreciation of the disclosure can be gained by taking the entire specification, claims, drawings, and abstract as a whole.

In one embodiment, a medical device for treating a bifurcated lumen is described. The medical device may include a catheter shaft having a proximal region, a distal region, and a longitudinal axis. A main balloon may be disposed about the distal region of the catheter shaft along the longitudinal axis. A secondary balloon may be coupled to the distal region of the catheter shaft and may be disposed offset from the longitudinal axis. The secondary balloon may have an inflatable portion including a first section and a second section where the first section may be more flexible than the second section.

In another embodiment, a method of forming a medical device for treating a bifurcated lumen is described. The method may include providing a balloon system disposed about a distal region of a catheter shaft, the balloon system including a first inflatable portion along a longitudinal axis of the catheter shaft and a second inflatable portion offset from the longitudinal axis of the catheter shaft, and modifying a region of the second inflatable portion of the balloon system to form a first section and a second section in the second inflatable portion having varying crystallinity and/or thickness, wherein the first section is more flexible than the second section.

In yet another embodiment, a medical device for treating a bifurcated vessel is described. The medical device may include a catheter shaft having a proximal region and a distal region. A first balloon may be disposed about the distal region of the catheter shaft. A second balloon may be coupled to the distal region of the catheter shaft. The second balloon may include a first section and a second section forming a pattern where the first section being more flexible than the second section. The first section and the second section may cause the balloon to collapse into a predetermined configuration having one or more pleats.

BRIEF DESCRIPTION OF DRAWINGS

The invention may be more completely understood in consideration of the following detailed description of various illustrative embodiments of the disclosure in connection with the accompanying drawings, in which.

DETAILED DESCRIPTION

The following detailed description should be read with reference to the drawings in which similar elements in different drawings are numbered the same. The drawings, which are not necessarily to scale, depict illustrative embodiments and are not intended to limit the scope of the invention.

Figure 1A:
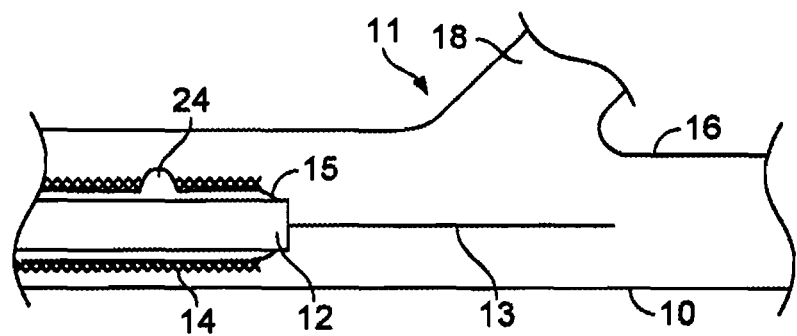
FIGS. 1A-1D are cross-sectional views illustrating delivery and deployment of a stent in a bifurcated lumen.
Figure 1B:
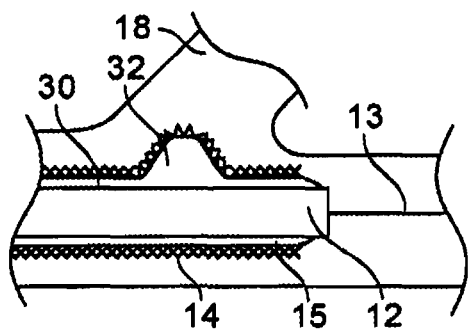
Figure 1C:
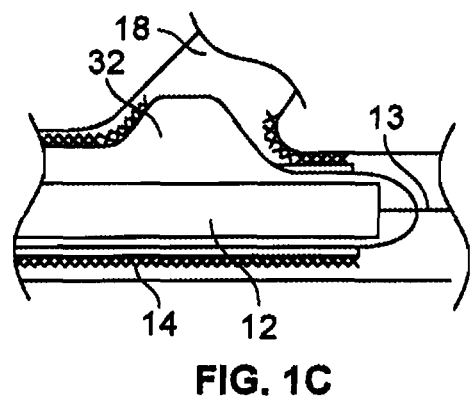
Figure 1D:
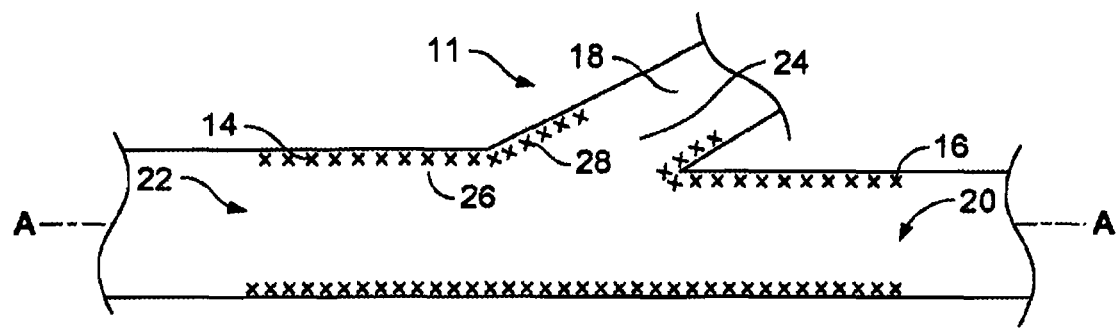

Referring to FIGS. 1A-1D, a body lumen 10, such as a blood vessel, that has a bifurcated region 11 is treated with a catheter 12 carrying a stent 14 over an inflatable balloon system 15. At the bifurcated region 11, the body lumen 10 forms a first branch 16 and a second branch 18. Referring particularly to FIG. 1A, the catheter 12 may be delivered through a tortuous pathway over a guidewire 13 to the treatment site about the bifurcated region 11. Referring as well to FIGS. 1B and 1C, the balloon system 15 is expanded to expand the stent 14 into contact with the wall of the body lumen 10. Referring to FIG. 1D, the balloon system 15 is then deflated and the catheter 12 withdrawn, leaving the stent 14 in place.

The stent 14 is arranged such that it can be placed in the bifurcated region 11. In this embodiment, the stent 14 includes distal 20 and proximal 22 openings as well as a side opening 24 such that the stent 14 will not obstruct the second branch 18 when it is positioned to span the bifurcated region in the first branch 16. In addition, the stent 14 includes a main axis region 26 which is along the axis A (shown in FIG. 1D) of the stent 14 and is expanded into contact with the first branch 16 and an off-axis region 28 that is expanded into contact with the second branch 18. The balloon system 15 likewise includes a main axis region 30, for expanding the main axis 26 of the stent, and an off-axis region 32 that expands the off-axis region 28 of the stent.

Figure 2A:
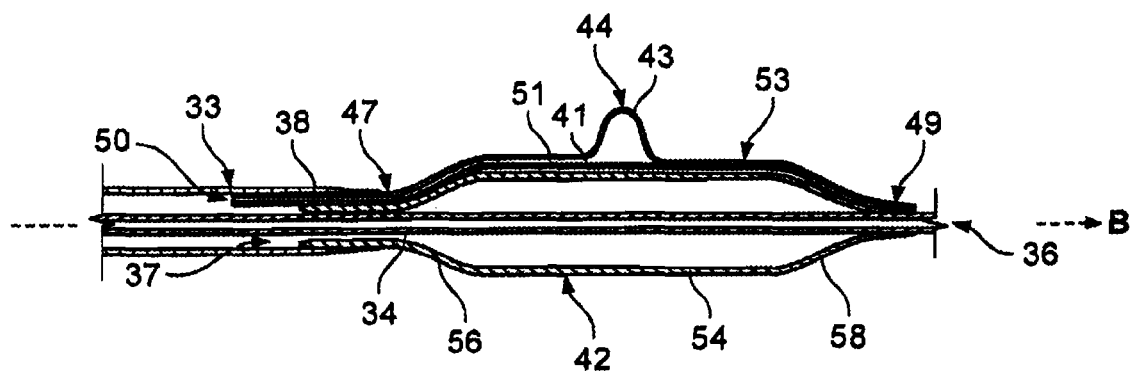
FIG. 2A is a cross-sectional view through a portion of a balloon catheter.
Figure 2B:
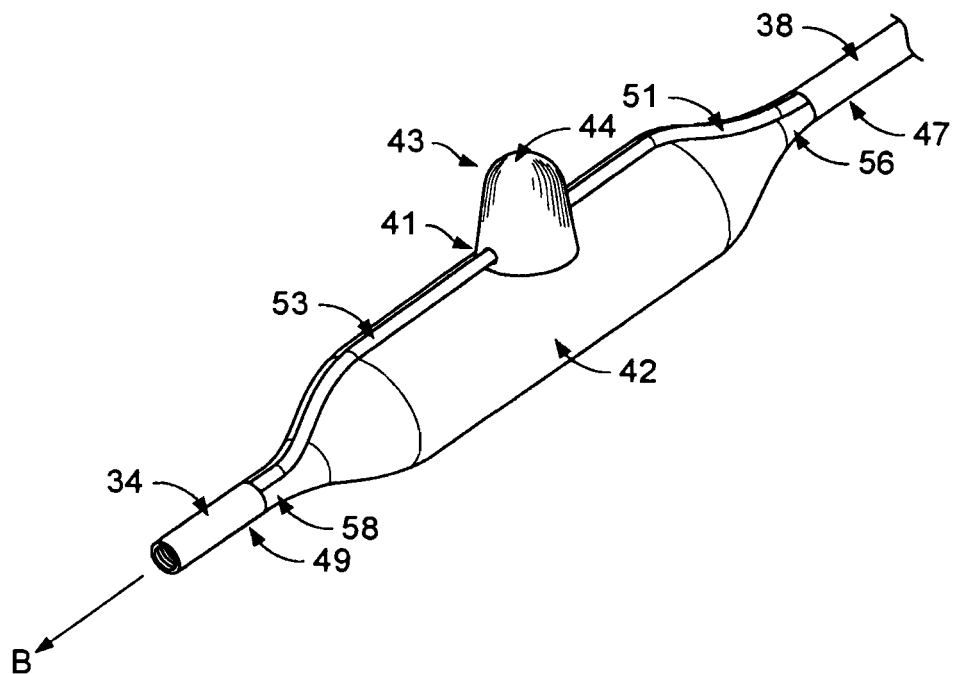
FIG. 2B is a perspective view illustrating a portion of a balloon catheter.

Referring to FIGS. 2A and 2B, a cross section and perspective view, respectively, of the distal end of a balloon catheter 33 suitable for placement in a body lumen 16. As in, for example, FIGS. 1A and 1B, the catheter 33 includes an inner shaft 34 defining a guidewire lumen 36, an outer shaft 38, and a dual balloon system. The concentric inner and outer shafts define an annular lumen 37 through which inflation fluid can be directed to the balloon system. The dual balloon system has a first, main balloon 42 including a region 54 that inflates in a generally cylindrical profile along the axis B of the catheter to expand the stent in the first branch 16 of the lumen. The main balloon 42 also includes proximal and distal sleeves or waists 56, 58, that are attached to the catheter. The system also includes a second, off-axis balloon 44 that expands off the axis of the catheter into the second branch 18 of the lumen. The off-axis balloon 44 extends along and around a portion of the main balloon and includes a base portion 41, an apex or dome 43, and proximal and distal sleeves 51, 53. The proximal sleeves of both balloons are attached at a region 47 of outer shaft 38 and the distal sleeves of both balloons are attached to a distal region 49 of the inner shaft of the catheter. The proximal sleeve 51 or leg of the off-axis balloon 44 provides a pathway 50 for inflation fluid to the interior of the balloon 44. In some cases, the distal sleeve 53 of the balloon 44 may be sealed to prevent inflation fluid from passing substantially beyond the off axis inflatable portion of the balloon. In this embodiment, inflation fluid delivered through the lumen 37 is directed to the main and off-axis balloons so that the balloons are inflated substantially simultaneously. In other embodiments, the off-axis and main balloons are arranged sequentially along the catheter axis. In other embodiments, the off-axis and main balloons can be provided on separate catheters that are delivered simultaneously or sequentially. In other embodiments, a single balloon is provided that has main and off-axis inflatable regions. Exemplary stent and catheter arrangements are described in U.S. Patent Application Publication No. 2005/0102023, and in U.S. Pat. Nos. 6,325,826; 6,210,429; 6,706,062; 6,596,020; and 6,962,602, all of which are incorporated herein by reference in their entireties.

Figure 3A:
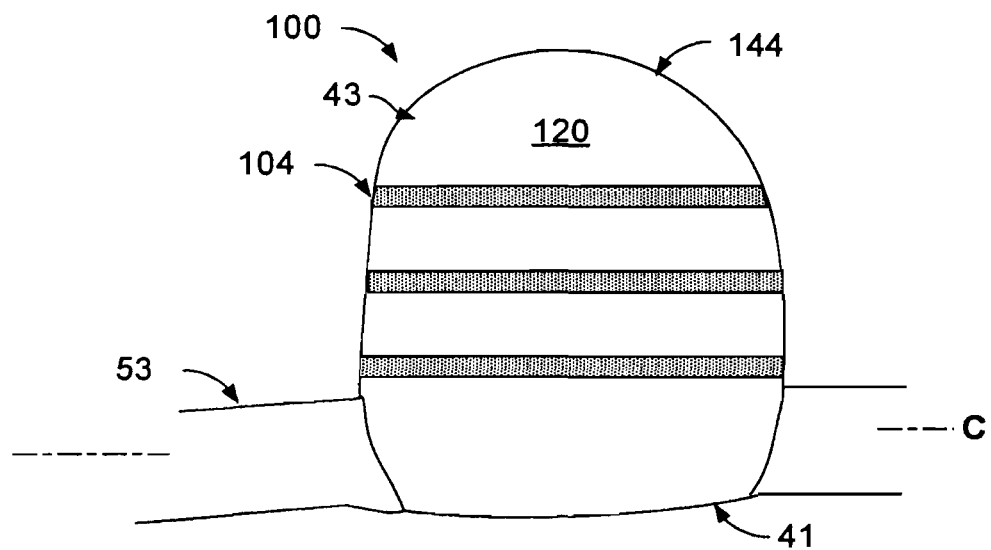
FIG. 3A is a side view of a balloon with ablated stripes in an inflated state.
Figure 3B:
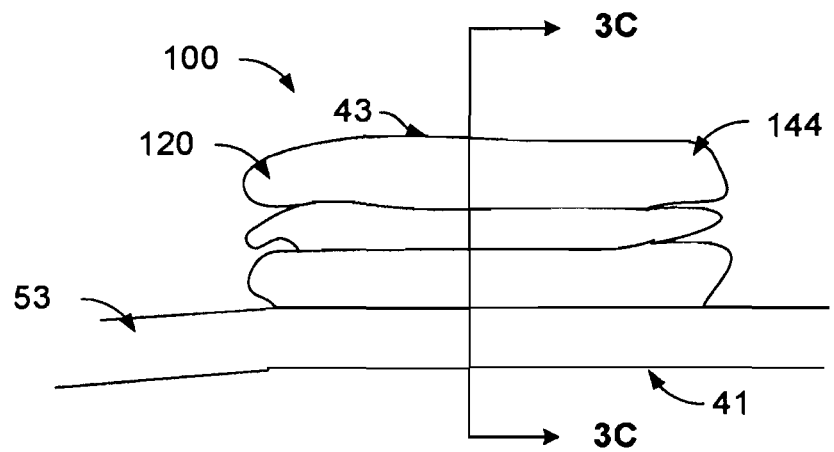
FIGS. 3B and 3C are side and cross-sectional views of a balloon with ablated stripes in a collapsed state.
Figure 3C:
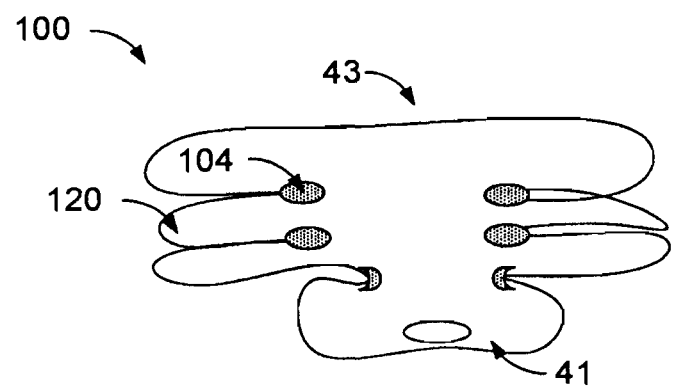

Referring to FIG. 3A an off-axis balloon 144 has flexible and less flexible portions. Specifically, the balloon 144 has regions 104 that are more flexible than the surrounding balloon material 120. Referring to FIGS. 3B and 3C, the more flexible regions 104 tend to fold inward upon deflation of the balloon 144.

Figure 4A:
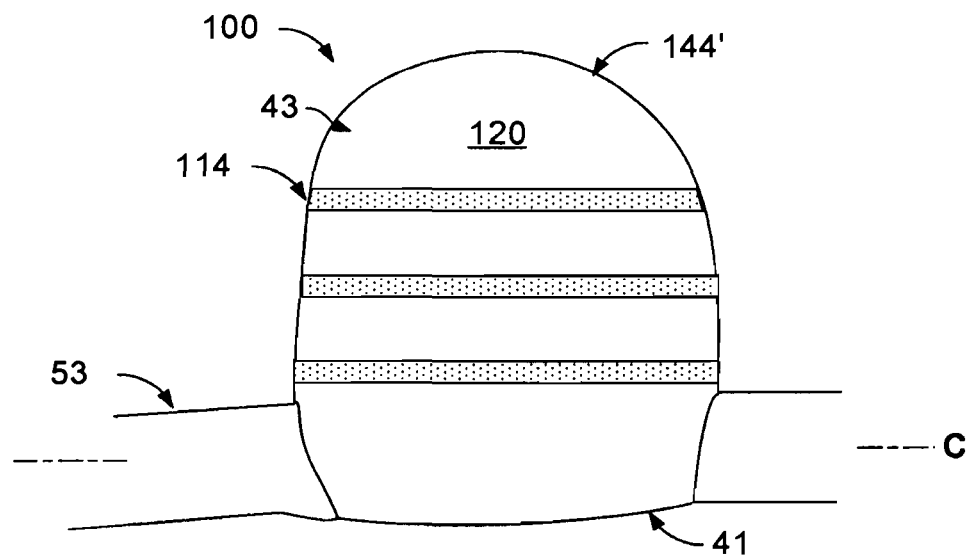
FIG. 4A is a side view of a balloon with stripes of increased crystallinity in an inflated state.
Figure 4B:
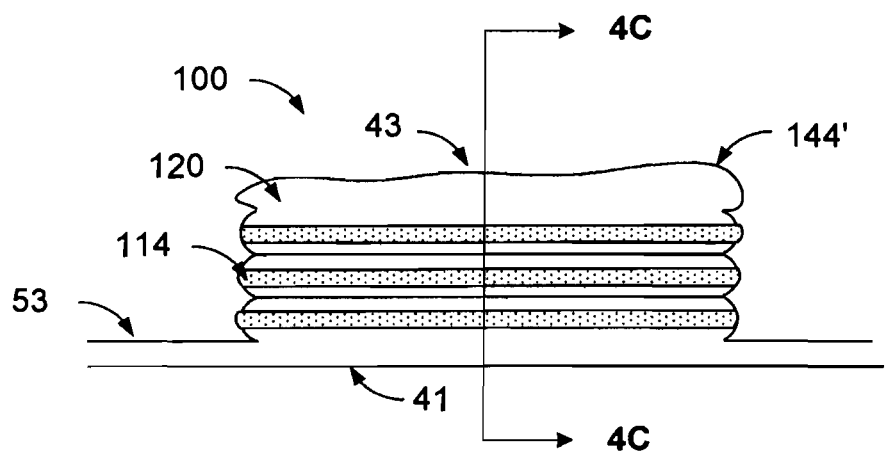
FIGS. 4B and 4C are side and cross-sectional views of a balloon with stripes of increased crystallinity in a collapsed state.
Figure 4C:
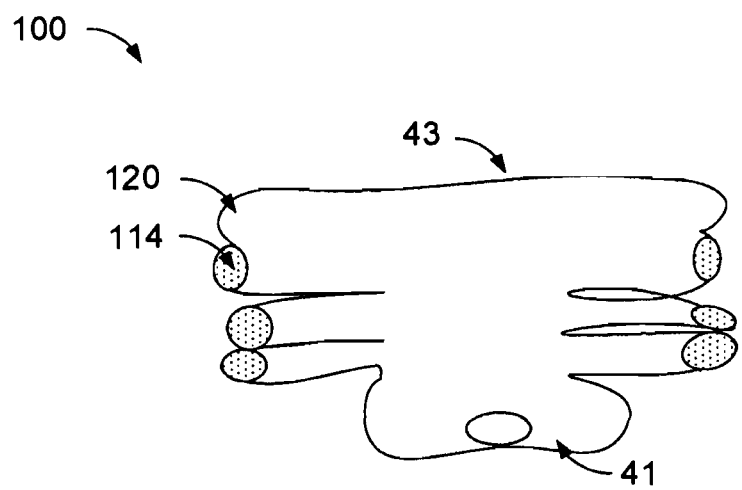

Referring to FIG. 4A, a balloon 144' has stiffer regions 114, as compared to the surrounding balloon material 120. Referring as well to FIGS. 4B and 4C, the stiffer regions 114 tend to stay on the outside of the balloon as it deflates and folds. The regions 104, 114 tend to stay on the outside of the balloon as it deflates and folds. The regions 104, 114 shown in FIGS. 3A et seq. and 4A et seq., respectively, form a pattern of stripes that are parallel to an axis C along which the distal sleeve 53 lies. A stripe pattern causes the dome of the balloon 114 to fold in an accordion manner, that is, the balloon 144 tends to form pleats as it collapses onto itself.

Figure 5:
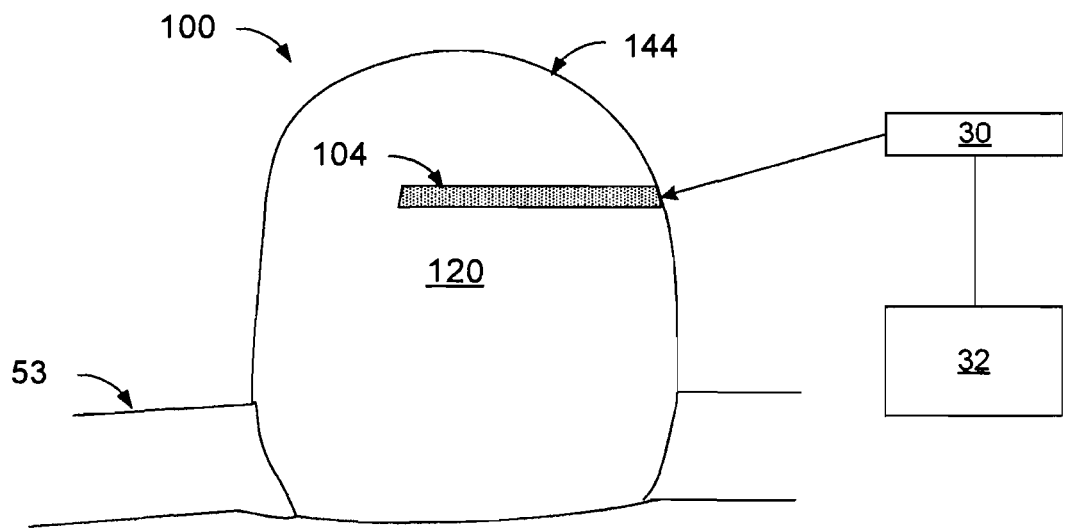
FIG. 5 is a schematic of a balloon being laser treated.

Referring to FIG. 5, the regions 104, 114 can be formed by treating the balloon material 120, such as by ablating or modifying the crystallinity of the balloon material by exposing the balloon to radiation, such as ultraviolet radiation. Ultraviolet radiation from a laser 30 can be modulated by controlled by a controller 32 to deliver selected energy to the exposed regions. For example, to ablate material the laser fluence is controlled to exceed the ablation threshold of the material. Chemical bonds are broken and the material is fractured into energetic fragments which leave the ablation zone. It is theorized that most of the energy is deposited in the ejected material so there is little thermal damage to surrounding materials. The high energy input to regions 104 removes some of the thickness of the material and therefore reduces the stiffness of these regions more than regions exposed to lower total energy or the unmodified polymer. The more flexible regions 104 tend to fold and collapse more readily as the balloon is deflated, forming valleys, as shown in FIGS. 3B and 3C.

To modify the crystallinity of the polymer without ablation, the laser fluence is controlled such that it is below the ablation threshold. In embodiments, the same laser 30 and controller 32 can be used to form regions 114 as used for forming regions 104. The regions 114 that are treated with the lower energy have increased crystallinity, which increases the stiffness or modulus of these regions. The increased stiffness causes the treated regions to be less flexible than the unmodified regions and thus the balloon is less likely to bend in the stiffer regions than in the unmodified regions. The stiffer regions 114 form the apexes of the accordion folds upon refolding as shown in FIGS. 4B and 4C. Whether the regions are ablated or have increased crystallinity, the balloon can have at least two modified regions. If the modified regions are in the form of stripes, the balloon can have two stripes or more, such as three stripes, as shown in FIGS. 3A and 4A, or even more stripes, such as four, five, size, seven or eight stripes. In embodiments, the balloon includes both regions 104, 114, e.g. in an alternating pattern.

The amount of ablation or degree of crystallinity modification can be selected to facilitate a desirable deflation profile. If the balloon is ablated, the amount of material removed can be for example, about 0.1-15%, such as 0.5 to 2.5% of the balloon wall thickness. If the balloon's crystallinity is modified without substantial ablation effects, the crystallinity of the polymer can be increased by about 2 to 90%, e.g., 2-5%, 5-10%, 10-20%, 20-40%, 40-60%, 60-70%, 70-80%, 80-90% or 20-80%, compared to the unmodified polymer. In some embodiments, the crystallinity percentage can be two, three or four times after modification than prior to modification. The thickness of the balloon in the crystallinity-modified regions and untreated regions can be substantially the same. With some materials, an increase in crystallinity is exhibited by nodules on the surface of the material. Crystallinity can be increased by heating the polymer material to between the glass transition temperature and the melt flow temperature. Within this temperature range, crystals begin to form, or crystals that were previously present grow larger. The amount of change in crystallinity can be controlled by controlling the energy delivered to the exposed regions, such as by controlling the time of exposure, the fluence and/or the wavelength of radiation. Crystallinity can be increased by increasing the exposure time at a low fluence. As noted above, the fluence threshold depends on the balloon material and on the type of wavelength of energy input into the material. Suitable UV lasers for treating the balloon have a wavelength between about 150-450 nm, such as 157, 193, 248, 308 or 351 nm. For treating a PET or a PEBAX® balloon with a 193 nm multigas laser, less than about 150 mJ/cm$^2$, such as between about 60-70 mJ/cm$^2$ will avoid ablating the balloon material. Other combinations of materials and lasers will have different thresholds of fluence to avoid ablation. Ultraviolet ablation is further described in U.S. Pat. No. 4,911,711. Suitable ablation and control systems are available from Coherent Lambda Physiks, in Goettingen, Germany. Crystallinity can be measured by WAX/SAX x-ray diffraction. Crystallinity measurements can be made at various vendors, such as the University of Minnesota Shepard characterization lab.

Crystallinity can be changed only on the surface or can be changed throughout the depth of the balloon wall. Suitable techniques for inputting heat into the balloon, such as UV lasers, affect primarily the surface of the balloon. For example, a UV laser may penetrate only part way into a polymer surface, such as 1-60 Angstroms into the balloon. Other heating techniques can penetrate more deeply into the material. With some methods of applying energy, the energy not only penetrates into the material, but radiates isotropically. This heating is considered to be massive or bulk heating of the material, because more than just the surface of the material is heated. A laser, such as a $CO_2$ laser, an IR laser, a YAG laser, a diode laser, excimer laser, or any another suitable photon source, or a heat stick, i.e., a conductive material connected to a heat cartridge, or an RF generator can be used to apply heat to the balloon. In the case of an RF generator, a jelly having metal particles can be applied to the regions to be treated. If a laser is used to apply heat to the balloon, the balloon can be filled with a fluid to absorb the heat and prevent other portions of the balloon from being simultaneously treated. As noted herein, the amount of crystallinity can be controlled, such as by controlling the amount of time that energy is input into the balloon or controlling the energy output by the energy input device. To focus the heat on particular regions of the balloon, a mask can be used or the device for applying the heat can be focused only in the region where crystallization is desired. With some methods of treating the balloon, the depth of the crystallization can determine whether the treated region ends up on the apex or the valley of a fold. Surface treatment with a UV laser tends to form treated regions that are in the valleys of the folds of the balloon, where treatment with a $CO_2$ laser or hot stick forms treated regions that are on the apex of the folds a balloon.

Flexibility or stiffness variations can also be created by other techniques, such as ion beam exposure and mechanically by cutting regions of the balloon wall. All of these techniques can be used in any combination to provide desired properties to the balloon. Ion beam treatment is further described in U.S. application Ser. No. 11/533,588, filed Sep. 20, 2006, and U.S. application Ser. No. 11/355,392, filed Feb. 16, 2006, both of which are incorporated herein by reference in their entirety. The treated regions can be formed by application of energy on the balloon directly or on a polymer tubular parison that is subsequently formed or blown into a balloon, e.g. by free inflation or blow molding. Balloon formation is described further in U.S. Pat. No. 4,963,313.

Figure 6:
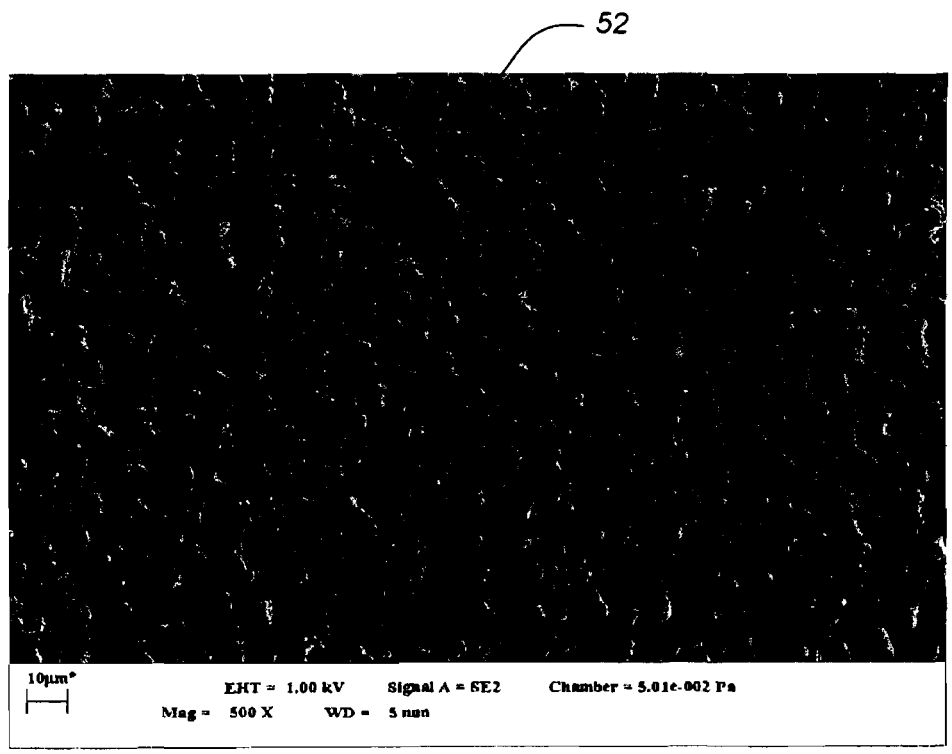
FIG. 6 is a scanning electron microscope image of a modified surface.

Referring to FIG. 6, an effect of some heat applications, such as application of UV laser, is to rearrange material at the surface of the balloon. A magnified view of a balloon surface that is crystallized using a UV laser shows nodules 52. The balloon is a TAXUS® Liberté™ OTW (PEBAX® 7233) polymer balloon available from Boston Scientific, Natick, Mass., and is exposed to UV radiation using a Lambda 210i, multigas UV excimer laser (available from Coherent Lambda Physiks, in Goettingen, Germany) operating at a wavelength of 193 nm with an attenuator set at 30 VA to achieve an output of 30 mJ/cm$^2$. Forming the nodules 52 does not remove polymer material from the balloon wall, but rearranges the material on the balloon surface and can reduce the effective wall thickness between the nodules. A non-treated balloon wall would appear smooth and free of nodules. Nodules 52 are observed when the balloon is treated with a UV laser, but are not observed with other treatments, such as $CO_2$ laser or hot stick. The UV laser treated regions also appear to be opaque, due to the surface modification.

Polymers suitable for forming the balloon include biaxially oriented polymers, thermoplastic elastomers, engineering thermoplastic elastomers, polyethylenes, polyethylene terephthalate (PET), polybutylenes, polyamides (e.g. nylon 66), polyether block amides (e.g., PEBAX®), polypropylene (PP), polystyrene (PS), polyvinyl chlorides (PVC), polytetrafluorethylene (PTFE), polymethylmethacrylate (PMMA), polyimide, polycarbonate (PC), polyisoprene rubber (PI), nitrile rubbers, silicone rubbers, ethylene-propylene diene rubbers (EPDM), butyl rubbers (BR), ethyl-ester thermoplastic elastomers (e.g., ARNITEL®), thermoplastic polyurethanes (PU) (e.g., those based on a glycol ether and an isocyanate, such as PELLETHANE®). In particular embodiments, a poly(ether-amide) block copolymer having the general formula

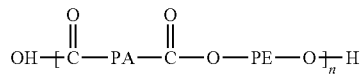

in which PA represents a polyamide segment, e.g., nylon 12, and PE represents a polyether segment, e.g., poly(tetramethylene glycol) is utilized. Such polymers are commercially available from ARKEMA under the tradename PEBAX®. The balloon can be formed of single polymer or of multiple polymers, e.g. by coextrusion.

Figure 7:
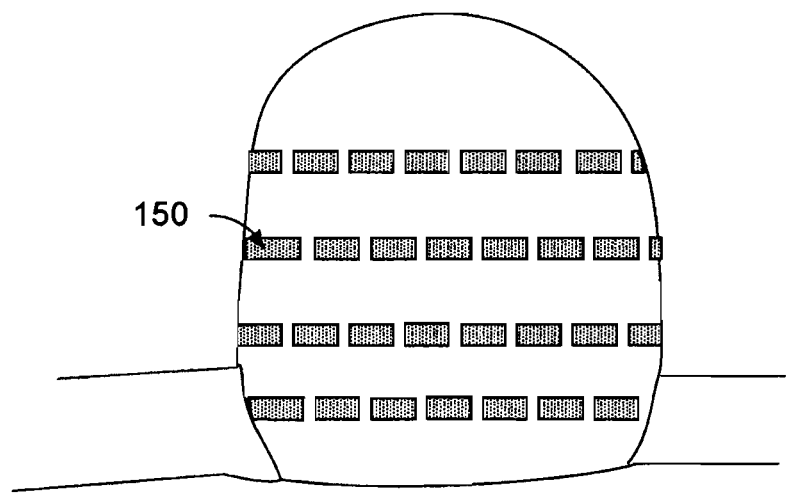
FIGS. 7-9 are alternative ablation or increased crystallinity patterns on inflated balloons.
Figure 8:
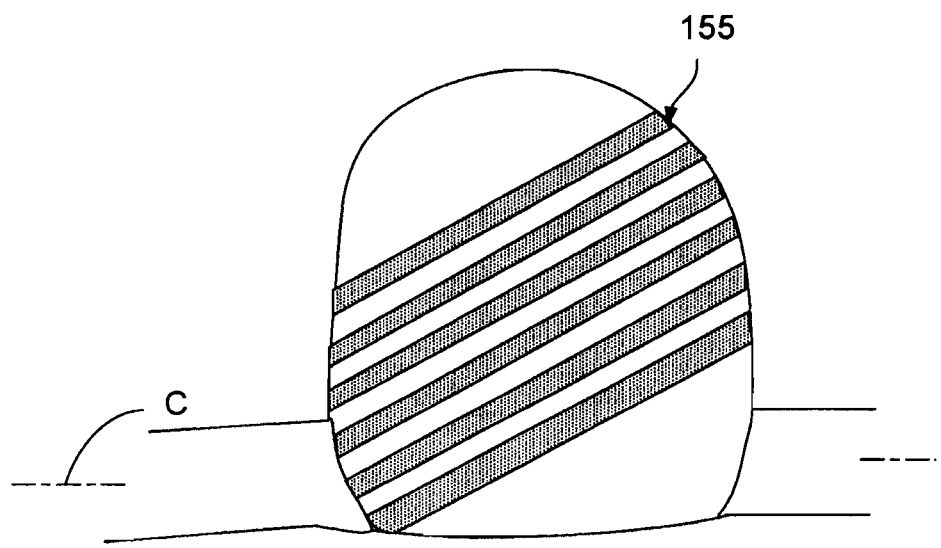
Figure 9:
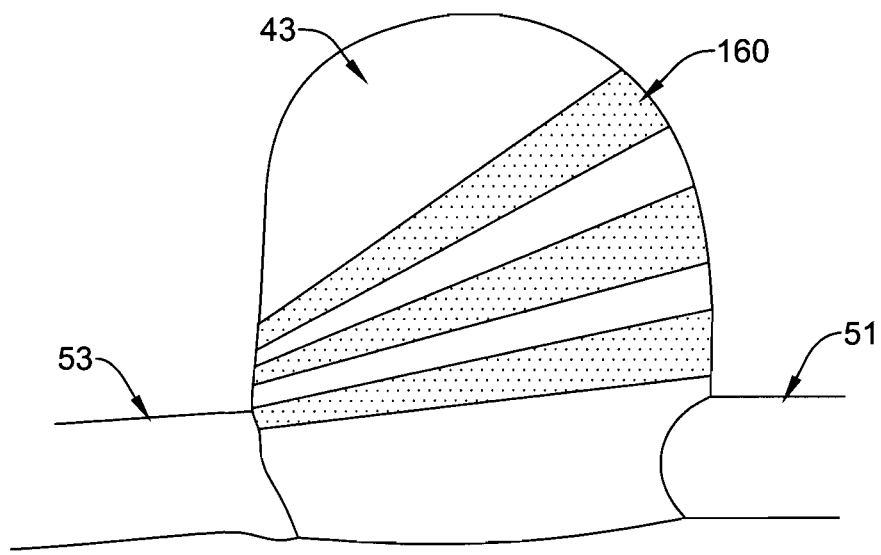

In addition to the linear treated regions described, the treated regions can be arranged in other configurations to enhance refolding. In some embodiments, the treated regions spiral around the dome of the balloon, so that the spiral winds around an axis that is perpendicular to the axis along which the sleeves extend. The spiral region can be one continuous region or can be series of non-contiguous regions that generally are in a spiral pattern. Referring to FIG. 7, the treated regions are not formed in a contiguous line, but are formed as a series of dots 150, dashes or shapes which together determine where the balloon will fold upon deflation. Referring to FIG. 8, the treated regions 155 can form stripes that are at an angle to the axis C of the sleeves, such as at an angle between about 30° and 60°, for example a 45° angle to the axis. Referring to FIG. 9, the treated region 160 can be wider on one side of the dome, that is on a side closer to a proximal sleeve 51 than on the other side of the dome, that is, the side closer to the distal sleeve 53. Regardless of the pattern, between about 20% and 80% of the balloon's dome can be treated to create regions of greater or lesser flexibility, such as 50±5% can be treated. In embodiments, the width of the treated regions is about 2 mm or less, such as about 0.1 to 0.5 mm. In some embodiments, ablation is performed only on the portion of the dome closest to the sleeves and not on the apex of the dome. In some bifurcation balloons, the apex of the dome tends to be the thinnest portion of the dome, having a thickness of only a few ten thousandths of an inch. Therefore, in such balloons, ablation may be avoided in the very thin parts of the balloon. Crystallinity modification, however, can be performed on the balloon dome portions closest to the sleeves or can be also on the apex of the dome.

Figure 10:
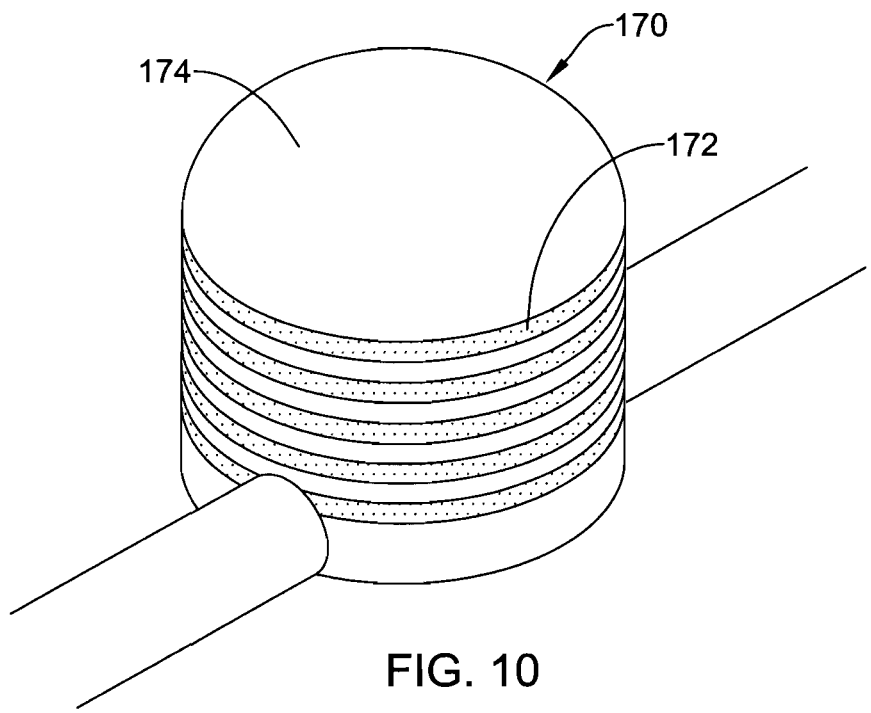
FIG. 10 is a perspective view of a balloon with ablated stripes.

Referring to FIG. 10, a bifurcation balloon 170 with five parallel treated regions 172 is shown. The top of the dome 174 is free of treated regions 172. As the balloon 170 deflates, the sides of the dome will collapse into pleats, causing the deflated balloon 170 to reduce down to a predictable shape so that the balloon 170 can be more easily pulled through a lumen than a non-treated balloon in a collapsed state.

Treating selected portions of a bifurcated balloon cause a bifurcation balloon to collapse in a predictable way when the balloon is deflated. The collapsed state can be selected so that the balloon folds in a compact manner. The more compact the balloon is when collapsed, the easier it may be to remove the balloon from a lumen after the balloon inflation and deflation. Moreover, a more compactly folded balloon may be less likely to catch on an expanded stent upon removal. Unlike cylindrical balloons, the bifurcation balloons tend to be in a naturally expanded state, even when they are not inflated. Thus, treating the balloons to enhance folding can add particular folding characteristics that the balloon would not otherwise have.

EXAMPLE

A 2.0×2.75 mm bifurcation PEBAX® polymer balloon made by Boston Scientific, Natick, Mass., is exposed to UV radiation using a Lambda LPX210i, multigas UV excimer laser (available from Coherent Lambda Physiks, in Goettingen, Germany) using an argon fluoride gas mixture operating at a pulse duration of 29 ns, a repetition rate of 25 Hz and at a wavelength of 193 nm with an attenuator set at 100% VA to deliver a fluence of 100 mJ/cm$^2$, which is above the ablation threshold of PEBAX®, which is around 60-70 mJ/cm$^2$. The homogenized beam from the laser is about 9 mm wide and about 9 mm long. Five parallel linear regions approximately 0.14 mm in width spaced equidistantly up the side of the dome of the balloon are exposed through a mask. Three of the regions are exposed at a shot spacing of 75 microns. Two of the regions are exposed at a shot spacing of 100 microns. The exposed regions became opaque.

Embodiments may include one or more of the following advantages. Balloon treatment of bifurcated lumens can be facilitated by reducing the likelihood that the balloon fold into a predictable configuration upon deflation. The profile of the side branch balloon on deflation after angioplasty or stent delivery can be reduced, e.g. by folding or forming into a desired, predictable configuration that facilitates withdrawal from a body lumen. It can require less withdrawal force to remove a balloon that has been folded compactly from a lumen than to remove a similar balloon that has not been folded compactly from the same lumen.

A number of embodiments of the invention have been described. Nevertheless, it will be understood that various modifications may be made without departing from the spirit and scope of the invention. It should be understood that this disclosure is, in many respects, only illustrative. Changes may be made in details, particularly in matters of shape, size, and arrangement of steps without exceeding the scope of the disclosure. The invention's scope is, of course, defined in the language in which the appended claims are expressed.

What is claimed is:

1. A method of forming a medical device for treating a bifurcated lumen, the method comprising:
providing a balloon system disposed about a distal region of a catheter shaft, the balloon system including a first inflatable portion along a longitudinal axis of the catheter shaft and a second inflatable portion offset from the longitudinal axis of the catheter shaft, the second inflatable portion of including a polymer; and
modifying a region of the second inflatable portion of the balloon system to form a first section and a second section in the second inflatable portion, the second section having a greater crystallinity than the first section such that the first section is more flexible than the second section, wherein the second inflatable portion includes a plurality of alternating first and second sections forming a striped pattern, wherein the second section stripes have a width of about 0.1 mm to about 0.5 mm, wherein the striped pattern is formed at an oblique angle to the longitudinal axis of the catheter shaft.

2. The method of claim 1 wherein the modifying includes directing radiation at the region of the second inflatable portion.

3. The method of claim 2 wherein directing radiation includes directing radiation that has a fluence below an ablation threshold to form the second section.

4. The method of claim 2 wherein directing radiation includes directing radiation that has a fluence above an ablation threshold to form the first section.

5. The method of claim 1 wherein the first section and second section cause the second inflatable portion to be collapsible into pleats.

6. The method of claim 1 wherein the second inflatable portion includes a polymer and the first section is an ablation region.

7. The method of claim 1, wherein the second section has a first width at a first side of the second inflatable portion and a second width at a second side of the second inflatable portion, the first width being greater than the second width.

8. A medical device for treating a bifurcated vessel, the medical device comprising:
a catheter shaft having a proximal region and a distal region and a longitudinal axis;
a first balloon disposed about the distal region of the catheter shaft along the longitudinal shaft; and
a second balloon coupled to the distal region of the catheter shaft and disposed offset from the longitudinal axis, the second balloon having an inflatable region including a plurality of sections, wherein alternating sections have different flexibility and/or stiffness such that one section is more flexible than adjacent sections and/or is stiffer than adjacent sections, wherein the plurality of sections form a pattern of alternating flexibility and/or stiffness;
wherein the pattern of alternating flexibility and/or stiffness in the sections is a pattern of stripes at an oblique angle to the longitudinal axis, wherein the pattern of stripes causes the second balloon to collapse into a predetermined configuration having one or more pleats.

9. The medical device of claim 8, wherein a first section is an ablation region and a second, adjacent section has a higher crystallinity than the first section.

10. The medical device of claim 8, wherein the stripes are at an angle of between about 30 degrees and about 60 degrees from the longitudinal axis.

* * * * *